(12) United States Patent
Carter et al.

(10) Patent No.: US 7,709,787 B2
(45) Date of Patent: May 4, 2010

(54) STEPPED ELECTRIC FIELD DETECTOR

(75) Inventors: Roger G. Carter, Rigby, ID (US); Shane A. Beard, Idaho Falls, ID (US); Debbie J. LaCroix, Idaho Falls, ID (US); Randall C. Johnson, Idaho Falls, ID (US)

(73) Assignee: The United States of America as represented by the Secretary of the Department of Commerce, Washington, DC (US)

( * ) Notice: Subject to any disclaimer, the term of this patent is extended or adjusted under 35 U.S.C. 154(b) by 176 days.

(21) Appl. No.: 11/892,610

(22) Filed: Aug. 24, 2007

(65) Prior Publication Data
US 2009/0050799 A1 Feb. 26, 2009

(51) Int. Cl.
H01D 55/44 (2006.01)
(52) U.S. Cl. .................................. 250/282; 250/286
(58) Field of Classification Search ............... 250/281, 250/282, 286, 287; 436/173
See application file for complete search history.

(56) References Cited

U.S. PATENT DOCUMENTS

| 3,522,425 | A |   | 8/1970  | Rich              |         |
|-----------|---|---|---------|-------------------|---------|
| 4,271,357 | A |   | 6/1981  | Bradshaw et al.   |         |
| 4,378,499 | A |   | 3/1983  | Spangler et al.   |         |
| 5,200,614 | A | * | 4/1993  | Jenkins           | 250/286 |
| 5,227,628 | A | * | 7/1993  | Turner            | 250/286 |
| 5,234,838 | A | * | 8/1993  | Bacon, Jr.        | 436/173 |
| 5,283,199 | A | * | 2/1994  | Bacon et al.      | 436/173 |
| 5,338,931 | A | * | 8/1994  | Spangler et al.   | 250/287 |
| 6,630,662 | B1|   | 10/2003 | Loboda            |         |
| 6,690,004 | B2|   | 2/2004  | Miller et al.     |         |
| 6,822,225 | B2|   | 11/2004 | Xu et al.         |         |
| 6,906,469 | B2|   | 6/2005  | Langford et al.   |         |
| 6,972,407 | B2|   | 12/2005 | Miller et al.     |         |

(Continued)

OTHER PUBLICATIONS

R.E. Clement, K. W. M. Siu, H. H. Hill, Jr. "Instrumentation for Trace Organic Monitoring". Book, Preface, Chapter 1, Index. 1992. Lewis Publishers. Chelsea, Michigan.

(Continued)

Primary Examiner—David A Vanore
Assistant Examiner—Johnnie L Smith
(74) Attorney, Agent, or Firm—Novak Druce & Quigg LLP

(57) ABSTRACT

An apparatus and method for measuring low or trace concentrations of compounds and mixture of gases. A method and apparatus of the invention permits separating ions of different mobilities by passing them through an abrupt change or step in electric field magnitude. By using the separation method, the compounds of interest may be measured with less interference from other compounds of the gas mixture, which reduces or eliminates the need for prior separation of the components of the gas mixture. Several embodiments of the invention are described including the use of current amplifiers on one, or more, parts of the apparatus. While a single screen can provide a chamber which is divided into two regions of different electric fields, it is within the scope of the invention to include multiple screens to provide several steps in the electric field permitting it to be possible to trap and measure ions with successively higher mobilities. The gases used include halogenated compounds, including fluorocarbons, and most preferable $SF_6$.

22 Claims, 3 Drawing Sheets

U.S. PATENT DOCUMENTS

| | | |
|---|---|---|
| 6,992,284 B2 | 1/2006 | Schultz et al. |
| 7,005,632 B2 | 2/2006 | Miller et al. |
| 7,071,465 B2 * | 7/2006 | Hill et al. .................... 250/286 |
| 7,105,808 B2 * | 9/2006 | Bromberg et al. ........... 250/287 |
| 7,417,222 B1 * | 8/2008 | Pfeifer et al. ............... 250/282 |

OTHER PUBLICATIONS

Timothy W. Carr. "Plasma Chromatography". Book, Preface, Chapter 1, Index. 1984. Plenum Press. New York, New York.

* cited by examiner

STEPPED ELECTRIC FIELD DETECTOR

BACKGROUND OF THE INVENTION

1. Field of the Invention

The present invention is directed to an apparatus and method for measuring low or trace concentration of compounds in a mixture of gases. The apparatus and method are used for separating ions of different mobilities by passing them through an abrupt change or step in electric field magnitude. By using the separation method and apparatus, compounds of interest may be measured with less interference from other components of a gas mixture which reduces or eliminates the need for prior separation of the components of the gas mixture.

2. Description of the Related Art

A large variety of methods and devices have been used to identify or quantify components of gaseous mixture. Gas chromatographs, mass spectrometers, ion mobility spectrometers, photo ionization detectors and many other such devices are currently employed to make these measurements. Applications for these are many and widely varied. They include monitoring of pollutants in air, analysis of gas mixtures in industrial applications, detection of explosives or toxins, locating leaks in piping, identification of unknown compounds, monitoring of chemical reactions and many more. However, the apparatus and method described herein provides yet another method of detecting and measuring ionizable compounds present in a gaseous mixture. It is sensitive enough to measure low or trace concentrations of some compounds and offers advantages over currently available detection technology under some conditions. It may be used as a stand alone detector or in combination with a separation device, such as, but not limited to, gas chromatography.

Over the years, several devices have been developed that use ion mobility to detect or measure compounds in a gaseous mixture. Ion mobility spectrometers (IMS) are one of the most common. Clement et al., "Instrumentation for Trace Organic Monitoring," (1992), Lewis Publishers, Inc., Chelsey, Mich. and Carr, "Plasma Chromatography," (1984), Plenum Press, New York, N.Y. gave descriptions of IMS operations. Basically, an IMS collects a time of flight spectrum of ions that have been allowed to drift through a region of constant electric field. One or more ion gates allows a short pulse of ions to enter the drift region and a spectrum is collected as a function of time after the gate is opened. The short gate open times allow the different ions to separate completely and form individual peaks in the spectrum.

Another type of common detector used with gas chromatographs is the Electron Capture Detector or ECD. In this detector, a radioactive element, such as Nickel-63 is used to create free electrons. Voltage is applied to two electrodes in the ECD in short pulses. This causes the free electrons to move to one of the electrodes and creates a detectible current. Pulses are kept short enough that the electrons, which have extremely high mobility, move to the collector, but the slower ions do not have time to reach the electrode. The introduction of compounds that capture electrons into the ECD reduces the number of free electrons and, thus, the current through the ECD is reduced. Although the ECD does use difference in mobilities to separate ions from free electrons, the ECD uses a pulsed electric field.

U.S. Pat. No. 3,522,425 to Rich describes an apparatus and method whereby ions of a particular mobility may be selectively separated from ions of different mobility in a gas stream and their abundance measured. This is accomplished by isolating an ion bearing sample of gas in a conduit through which the gas flows at a predetermined rate and applying a predetermined electric field thereto so that the ions of desirability are retained while ions of different mobilities are removed, then discharging the retained ions and measuring the thus obtained current pulse.

U.S. Pat. No. 4,271,357 describes a device used to detect trace quantities of chemicals in air. It works by using a gas jet to carry ions through a region of opposing electric field. The lower mobility ions are carried through the region while the higher mobility ions move upstream in the jet and eventually wander out of the gas jet. However, each of these prior art disclosures have certain drawbacks which are overcome by the claimed apparatus and method. These and other advantages of the invention will become apparent with reference to the following description.

One of the problems with detection of trace levels of compounds in gases is that the detectors often respond to components of the original gas mixture. For example, halogenated compounds readily form negative ions by capturing free electrons. Their presence can then be detected by allowing them to discharge on an electrode and measuring the resulting current or by measuring the decrease in current from the free electrons. The difficulty with this measurement technique is that oxygen will also capture electrons and form negative ions. When measuring halogenated compounds in air, the oxygen, which makes up 21% of air, typically saturates the detectors so the halogenated compounds can not be detected. This requires the halogenated compounds to be separated from the oxygen prior to being introduced into the detector. However, oxygen has a higher mobility than most halogenated compounds, so the electric fields in the SEFD may be adjusted to trap the halogenated compounds at the screen while allowing the oxygen to continue to move upstream. As can be seen from the following disclosures, the invention is capable of detecting very low concentrations of halogenated compounds in air without any prior separation.

SUMMARY OF THE INVENTION

When exposed to an electric field, ions attempt to move in response to the electrostatic force exerted on them. Ions in a gaseous mixture cannot move freely in the electric field because interactions with the other molecules interfere with their movement. This competition between the accelerating force in the electric field and the resistance to movement caused by molecular interactions results in a constant drift velocity for the ions under steady state conditions. All ions of the same type will move with the same drift velocity while different ions will have a different drift velocity. Typically, smaller, lower mass ions have a higher drift velocity since they interact less with other gas molecules. Ions with higher drift velocities are said to have higher mobilities. The apparatus described herein, is referred to in this document as a Stepped Electric Field Detector (SEFD), which exploits differences in ion mobilities to preferentially detect ions of lower or higher mobility. It operates by ionizing the molecules present in the gas mixture and exposing them to an electric field that causes them to move upstream in a flowing gas stream. As they move upstream, the ions pass through an electrically conductive screen or other porous conductor placed across the flow path. On the upstream side of the screen, the electric field is significantly less than on the downstream side. The magnitude of the electric field in this region is set so that the drift velocity of the ions of interest is less than or only slightly greater than the flow velocity of a gas, while the higher mobility ions still have a drift velocity higher than the gas flow velocity. Thus, the lower mobility ions either stop at the screen or move very slowly through it, making it very probable that they will collide with the screen and give up their charge which results in a measurable electric current proportional to the concentration. The higher mobility ions move much more quickly through the screen and so have a much lower probability of colliding with and discharging on the screen. It is much more probable that the higher mobility ions will continue upstream and will give up their charge on a conductive plate at the upstream end of the detector. This also results in a measurable current proportional to the concentration of the high mobility ions.

The present apparatus and method is sensitive enough to measure low or trace concentrations of some compounds and offers advantages over currently available detection technologies under some conditions. It is capable of detecting very low concentrations of halogenated compounds in air without any prior separation. It may be used as a stand alone detector or in combination with a separation device such as, but not limited to, gas chromatography. The invention will be better understood by reference to the appended drawings and the detailed description of the preferred embodiments.

BRIEF DESCRIPTION OF THE DRAWINGS

The invention will now be explained and objects, other than those set forth above, will become apparent when consideration is given to the following detailed description which makes reference to the annexed drawings herein.

DESCRIPTION OF THE PREFERRED EMBODIMENTS

Figure 1:
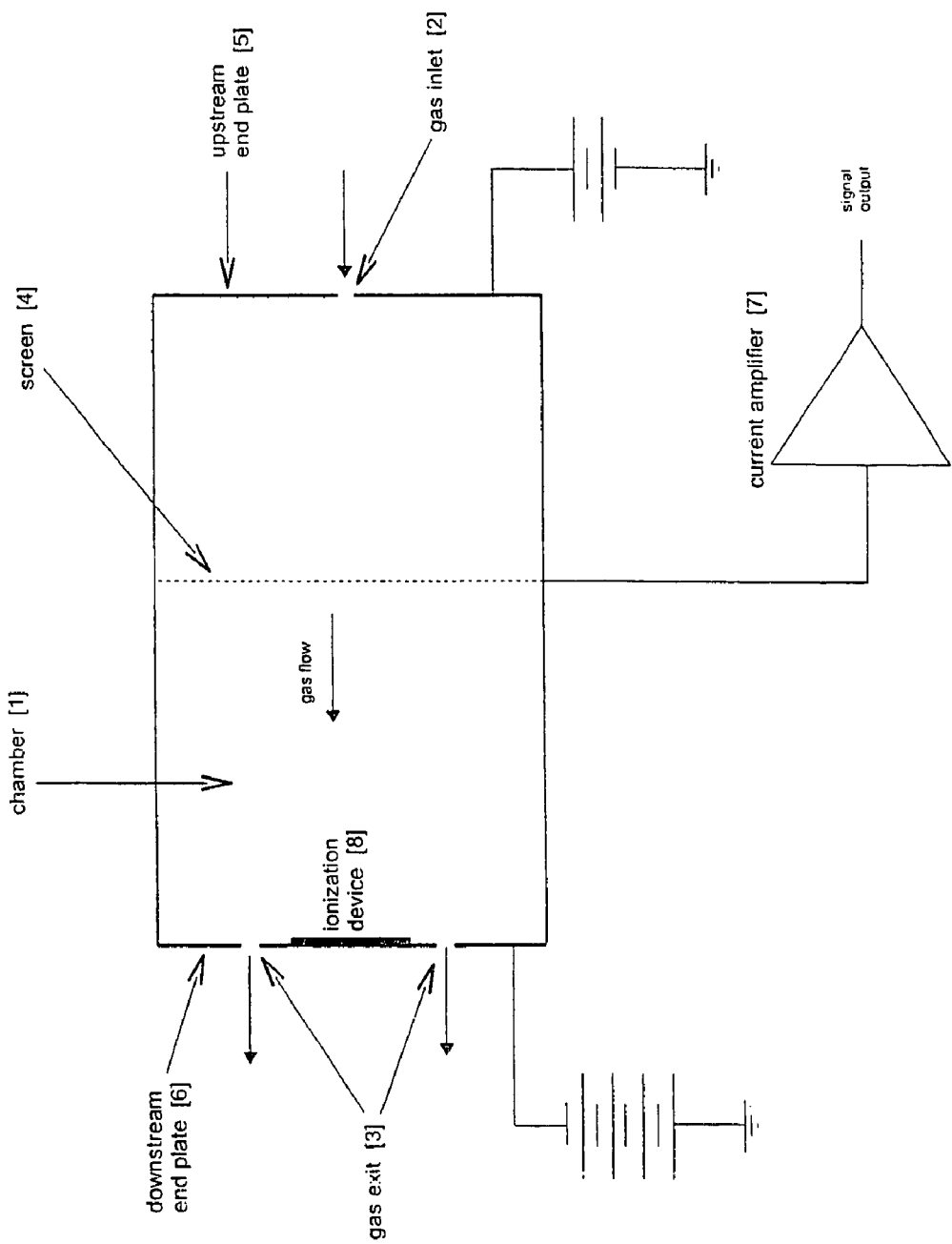
FIG. 1 is a schematic view of a stepped electric field detector (SEFD) as described herein configured for detecting low mobility ions.

With reference to FIG. 1, the apparatus shows one embodiment of the invention in which an apparatus and method are used to measure components of gaseous mixtures. The apparatus comprises a chamber 1 having a gas inlet 2 at one end and a gas exit 3 at the opposite end. The current embodiment of the device uses a cylindrical chamber, but chambers with cross-section geometries other than circular could be used as well.

Gas inlets 2 and exits 3 may be any type of opening or set of openings in the chamber that allows gas to flow in or out of the chamber. They may include baffles, screens or other devices to create a more uniform gas flow or control the gas flow in any manner. Gas flow through the chamber from the inlet to the exit may be provided by pumps, fans, blowers, compressors, compressed gas tanks or any other device that could generate a constant flow of gas. Gases of particular interest includes halogenated compounds, including fluorocarbons, such as Freon, and most particularly $SF_6$.

The chamber 1 is divided into two regions by an electrically conductive screen 4. A grid of wires, a set of parallel wires, a porous plate or any similar divider may be used in place of the screen 4. Requirements for this divider are that it is electrically conductive and allows gas to flow through without significantly changing the gas velocity. A conductive ring will actually work, although it may not be as efficient as other arrangements. For convenience, in the following descriptions, the divider will be referred to simply as the screen.

When configured for the detection of low mobility ions as shown in FIG. 1, the screen 4 is connected to the input of a sensitive current amplifier 7 which produces an output voltage proportional to the electric current.

The end of the chamber where the gas inlet is, or upstream end, is terminated by an electrically conductive plate, screen, grid or other device that provides an approximately planar electrically conductive surface. For convenience, this electrical conductive surface is referred to hereinafter as end plate 5. This end plate 5 is electrically insulated from screen 4. A voltage is applied to end plate 5 to create an electric field between end plate 5 and screen 4. This voltage may be created with a suitable battery, power supply or other similar device. This voltage may be adjusted to maximize the separation of the lower mobility ions to be detected on screen 4 and higher mobility ions to be detected on the end plate 5. Typically, the drift velocity of the ions to be trapped on the screen 4 should be less than or just slight greater than the gas flow velocity while the drift velocity of the high mobility ions to be discharged on the end plate 5 should be significantly greater than the gas flow velocity.

The end of the chamber where the gas exits, or downstream end, is terminated by another plate, screen or other device that provides an approximately planar electrically conducting surface. For convenience, this electrically conductive surface will be hereinafter described as end plate 6.

Downstream end plate 6 is also electrically insulated from screen 4. The voltage is applied to end plate 6 to create an electric field between end plate 6 and the screen 4. This voltage may be created with suitable batteries, power supply or similar devices. The plurality and magnitude of this voltage should be adjusted such that all ions of the polarity of interest will drift toward screen 4 with a drift velocity significantly greater than the gas flow velocity. Since the electric field on the downstream side of the screen 4 is greater than the electric field on the upstream side of screen 4, an abrupt change or step in the electric field is created at the screen 4.

The output of the current amplifier 7 may be connected to a volt meter, chart recorder, oscilliscope, analog to digital convertor or any other voltage display or recording device.

An ionization device 8 is placed on the downstream end of the chamber. This may be a radioactive material, a corona discharge device, a photo-ionization or chemical ionization device, or any other device that will ionize the molecules of interest. The ionization may take place in the chamber or a stream of ionized molecules may be injected into the chamber near the downstream end.

Compounds to be detected may be included as part of the gas flowing through the chamber, mixed with this gas prior to its entering the chamber or introduced into the chamber separately through another port (not shown). If the flow of sample gas is small compared to the flow of primary gas flowing through the chamber, it may be introduced into the chamber at any point without disrupting the operation of the SEFD.

Figure 2:
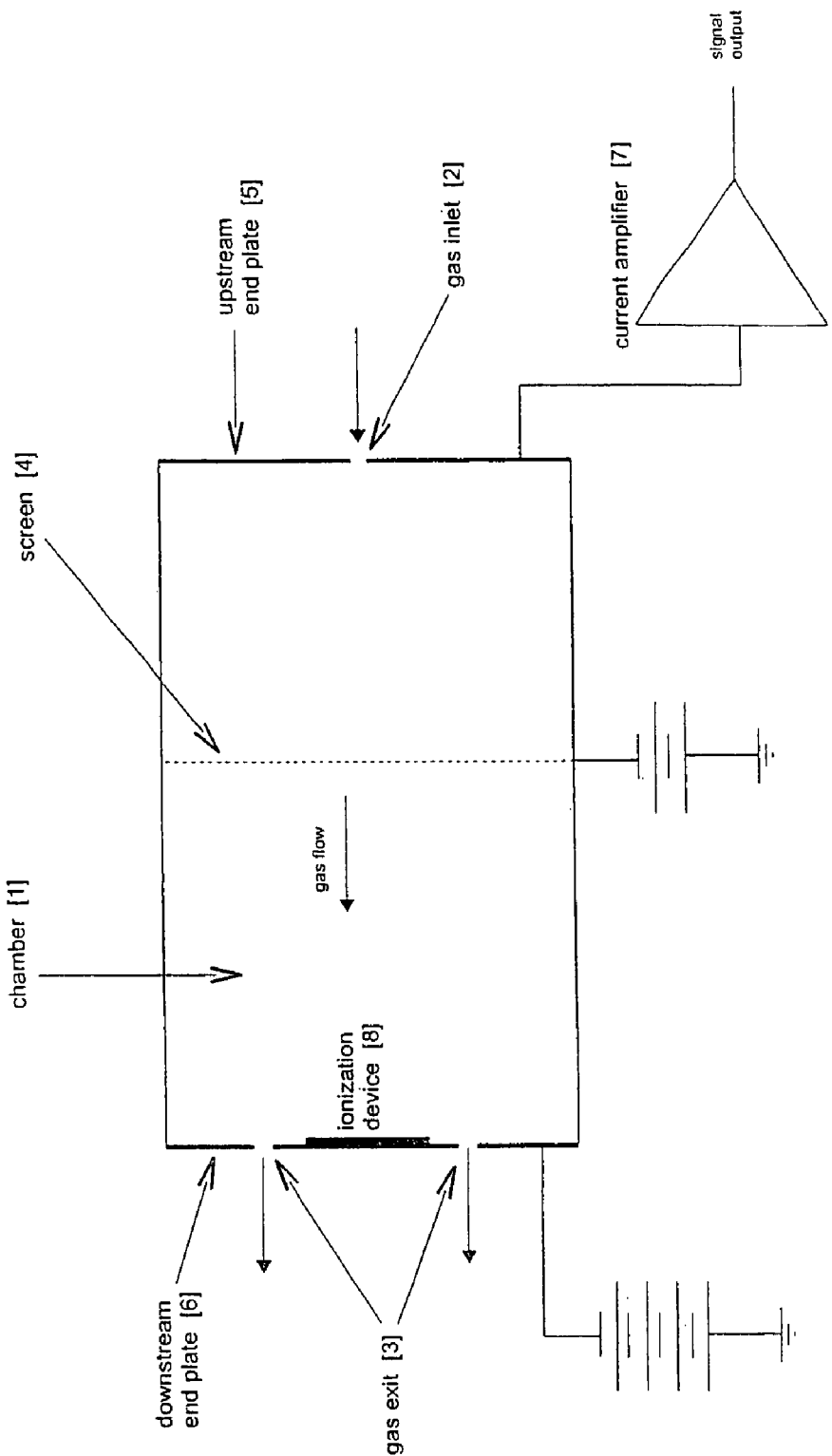
FIG. 2 shows the SEFD configured to measure high mobility ions that have been separated from low mobility ions.

FIG. 2 shows the SEFD configured to measure high mobility ions that have been separated from low mobility ions. As can be seen therein, current amplifier 7 is applied to end plate 5 rather than to screen 4 as in FIG. 1.

Figure 3:
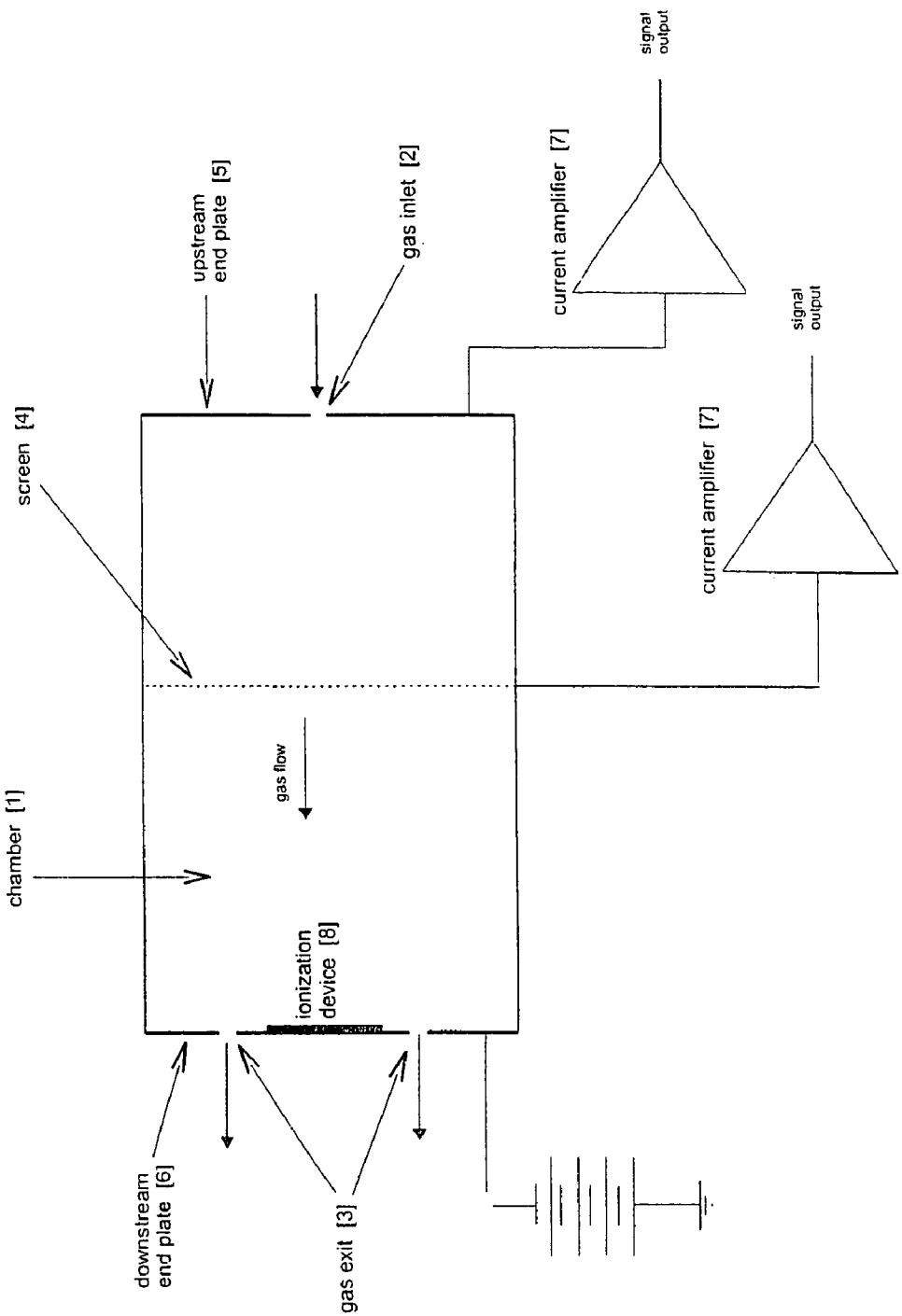
FIG. 3 shows a dual current amplifier configuration that allows simultaneous measurement of both the low and high mobility ions.

In FIG. 3, current amplifiers 7 are applied both to the end plate 5, as well as screen 4, thereby modifying the embodiments of FIGS. 1 and 2. The dual current amplifier configuration of FIG. 3 allows simultaneous measurement of both the low mobility and high mobility ions. This configuration requires that the current amplifier provide the proper voltage bias to the screen 4 and end plate 5 on their inputs.

A further variant of the invention shown in FIGS. 1-3 is to place multiple screens (not shown) in the SEFD. If a screen is connected to a current amplifier and biased at voltages necessary to create appropriate steps in the electric field, it would be possible to trap and measure ions with successively higher mobilities. The principal of operation remains unchanged in such an embodiment and this is just a variation of the previously disclosed embodiments of the invention.

ADVANTAGES OF THE INVENTION

The SEFD is unique in its simplicity and its ability to both separate and detect compounds. It has no moving parts, no ion gates and no varying or switching voltages. The only electronics are the two constant voltage supplies on the respective ends of the cylinder and the current amplifier. Because it does not make time dependent measurements of rapidly changing events, the current amplifier may be designed with a slow response time that matches the time required for the gas to be flushed out of the chamber. This allows more flexibility in gain and noise characteristics. Furthermore, as the SEFD operates continually without stopping, switching or trapping the ion flow, 100% of the ions enter the measurement region which results in better efficiency and lower limits of detection. Many devices based on ion mobilities use ion gates that only allow a small fraction of the created ions to enter the measurement region. Furthermore, simplicity of the disclosed apparatus allows it to be miniaturized and/or manufactured very inexpensively. Another advantage of the SEFD is the capability to detect either positive or negative ions depending only on the polarity of the applied voltages. Other detectors, such as the ECD, are limited to ions of one polarity.

The SEFD provides both separation and detection in one small package and maybe configured to detect compounds in air without any additional separation. This has immediate applications in atmospheric monitoring. The SEFD may be also be configured to monitor for explosives or toxins that would indicate terrorist activities. It may also be used to monitor industrial processes, check for leaks, monitor for accidental releases of chemicals in factories, monitor for pollutants, check for the presence of pesticides and many other commercial applications.

The SEFD may also be configured as a gas chromatograph detector where it could replace the ECD in many applications while offering the ability to detect positive ions which the ECD cannot do. Its integral separation capabilities may provide better detection of co-eluding peaks.

DESCRIPTION OF PARTICULARLY PREFERRED EMBODIMENTS

An SEFD prototype currently in use is configured to measure low mobility ions as shown in FIG. 1. The chamber 1 is constructed of a polytetrafluoroethylene material, commercially known as "TEFLON." It is cylindrical and one inch in diameter. Screen 4 is a stainless steel screen with 72% open area. It is approximately 0.375 inch from the screen to the downstream end of chamber 3. The downstream end of the chamber is formed by a metal tray containing a radioactive foil which serves as the ionization device 8. The tray is about 0.125 inch deep so that the radioactive foil is about 0.5 inch from the screen. The upstream end of the chamber is about 0.125 inch from the center screen and is formed by a second stainless steel screen with about 30% open area. The gas is introduced into the chamber through the screen.

This embodiment of the SEFD has been used to measure sulfur hexafloride ($SF_6$) in air. The downstream end was biased at −105 volts, the upstream end as +1.5 volts and the gas flow rate was set to approximately 500 ml/minute. In this configuration, the SEFD is capable of detecting less than one part per million of $SF_6$ in air. However, it is within the skill of the art that the parameters given here may be adjusted to optimize operation for different purposes.

From all the foregoing, it will be apparent to those skilled in the art that many minor changes may be made in the specific form of the apparatus and method disclosed herein, which are provided only for purpose of illustration and not by way of limitation. It is, therefore, not intended that the scope of the invention be limited in any way through various modifications of the apparatus and method as will become apparent by those of ordinary skill in the art upon reading the instant disclosure.

We claim:

1. An apparatus for detecting ionized compounds in a gaseous mixture comprising:
    (a) a chamber through what a gaseous mixture containing the ionized compounds is passed;
    (b) an electric field created in the chamber by placing conductive or semi-conductive elements at both inlet and outlet ends of the chamber, each of said elements connected to an electric voltage source;
    (c) dividing the chamber into at least two regions by placing at least one permeable conductor or semi-conductor across the chamber connected to a voltage source which is different from the voltage source connected to said elements, thereby creating an abrupt change (or step) in electric field strength so that the field strength in a region of the chamber on one side of the divider is significantly different from the electric field strength in the region of the chamber on the other side of the divider while maintaining the electric field parallel in each of the regions.

2. The apparatus of claim 1, further comprising an ionization device with said chamber.

3. The apparatus of claim 2, wherein said ionization device is adjacent said outlet end.

4. The apparatus of claim 1, further comprising a current amplifier electrically connected to said permeable conductor or semi-conductor.

5. The apparatus of claim 4, wherein said permeable conductor or semi-conductor is a screen.

6. The apparatus of claim 1, comprising at least a second permeable conductor or semi-conductor positioned in said chamber, said at least a second conductor or semi-conductor being connected to a source of voltage different from the first conductor or semi-conductor.

7. The apparatus of claim 6, further comprising a current amplifier electrically connected to each of said at least one and said second permeable conductor or semi-conductor.

8. The apparatus of claim 1, further comprising a current amplifier attached to said inlet end.

9. The apparatus of claim 1, further comprising a current amplifier attached to said inlet end and said at least one permeable conductor or semi-conductor.

10. The apparatus of claim 1, wherein at least one of the inlet or outlet ends comprise at least one member selected from the group consisting of baffles and screens.

11. The apparatus of claim 4, further including at least one voltage display or recording device selected from the group consisting of a voltmeter, chart recorder, oscilloscope and analog to digital converter.

12. The apparatus of claim 8, further including at least one voltage display or recording device selected from the group consisting of a voltmeter, chart recorder, oscilloscope and analog to digital converter.

13. A method of detecting ionizable compounds present in a gaseous mixture, said method comprising:

generating a flow of gas containing said ionizable compound through a chamber from an inlet end to an outlet end thereof;

passing the gas through an electrically conductive or semi-conductive divider element positioned within said chamber;

providing a voltage on said divider element and both ends of the chamber such that an abrupt change (or step) in the electric field strength is created at the divider element so that the electric field strength in a region of the chamber on one side of the divider is significantly different from the electric field strength in the region of the chamber on the other side of the divider while maintaining the electric field strength parallel in each of the regions; and detecting the ions by measuring the electric current generated by ions releasing the charge on the divider element or at the ends of the chamber.

14. The method of claim 13, further comprising providing a current amplifier on said divider.

15. The method of claim 13, further comprising providing a current amplifier on said inlet end.

16. The method of claim 13, further comprising providing several dividers in said chamber and providing each of the dividers with a voltage different from the voltage of each other divider as well as from the inlet and outlet ends such that an abrupt change (or step) in the electric filed strength is created at each divider.

17. The method of claim 13, comprising creating ionized molecules outside the chamber.

18. The method of claim 13, comprising creating ionized molecules within the chamber.

19. The method of claim 13, wherein the gaseous mixture comprises air.

20. The method of claim 13, wherein the gas comprises a halogenated compound.

21. The method of claim 20, wherein the gas is a fluorocarbon.

22. The method of claim 20, wherein the gas is $SF_6$.

* * * * *